United States Patent [19]
Krause

[11] Patent Number: 5,483,027
[45] Date of Patent: Jan. 9, 1996

[54] EARPLUG WITH FORM-FITTING FLUID CHAMBERS

[76] Inventor: Ward B. Krause, 10518 Ni River Dr., Spotsylvania, Va. 22553

[21] Appl. No.: 294,946

[22] Filed: Aug. 24, 1994

[51] Int. Cl.$^6$ ........................................ A61B 7/02
[52] U.S. Cl. .......................................... 181/135; 128/865
[58] Field of Search .................................. 181/130, 135; 128/864, 867, 865; 2/209

[56] References Cited

U.S. PATENT DOCUMENTS

| | | |
|---|---|---|
| Re. 29,487 | 12/1977 | Gardner, Jr. . |
| 1,344,935 | 6/1920 | Baum . |
| 2,246,736 | 8/1938 | Knudsen . |
| 2,437,490 | 6/1942 | Watson et al. . |
| 2,785,675 | 3/1957 | Berkman . |
| 2,785,676 | 3/1957 | Berkman . |
| 2,824,558 | 2/1958 | Michael et al. . |
| 2,850,012 | 9/1958 | Becker ........................... 181/135 |
| 2,876,767 | 3/1959 | Wasserman . |
| 3,736,929 | 6/1973 | Mills . |
| 4,060,080 | 11/1977 | Akiyama . |
| 4,434,794 | 3/1984 | Leight . |
| 4,540,063 | 9/1985 | Ochi et al. . |
| 4,582,053 | 4/1986 | Wilson . |
| 5,080,110 | 1/1992 | Weldon et al. . |
| 5,195,539 | 3/1993 | Dyrud et al. . |
| 5,249,309 | 10/1993 | Berg et al. . |

FOREIGN PATENT DOCUMENTS

1731214A1  11/1988  U.S.S.R. .

OTHER PUBLICATIONS

Shell Chemical Company Technical Bulletin SC:1032–88, Kraton Thermoplastic Rubber Medical Products (May 1988).

Provisional Technical Bulletin for Kraton G–2706, GLS Plastics (Aug. 1989).

Santoprene, Monsanto Elastomers Brochure TPE–74–01 (date unknown).

*Primary Examiner*—Khanh Dang
*Attorney, Agent, or Firm*—Banner & Allegretti, Ltd.

[57] ABSTRACT

A bi-directionally insertable elastomeric ear plug for sealing an ear canal has an outer body defining two identical expansible and collapsible fluid chambers. A fluid, preferably air, is sealed within the outer body, and a passageway is defined between the two fluid chambers for selectively placing the chambers in fluid communication with each other. An elastically displaceable wall bounding the passageway acts as a two-way pressure responsive valve operative to close the passageway and thereby maintain an equilibrium condition with one of the chambers expanded and the other collapsed, and to temporarily open the passageway when one of the chambers is squeezed. The collapsed chamber is insertable into an ear canal with the aid of an elongated semi-rigid core member extending within the outer body. Thereafter, the expanded chamber can be squeezed to expand the collapsed chamber inside of the ear canal to obtain a comfortable yet tight form-fitting seal.

30 Claims, 5 Drawing Sheets

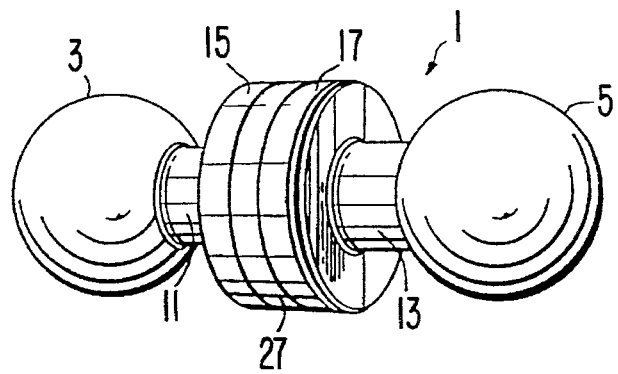
FIG. 1
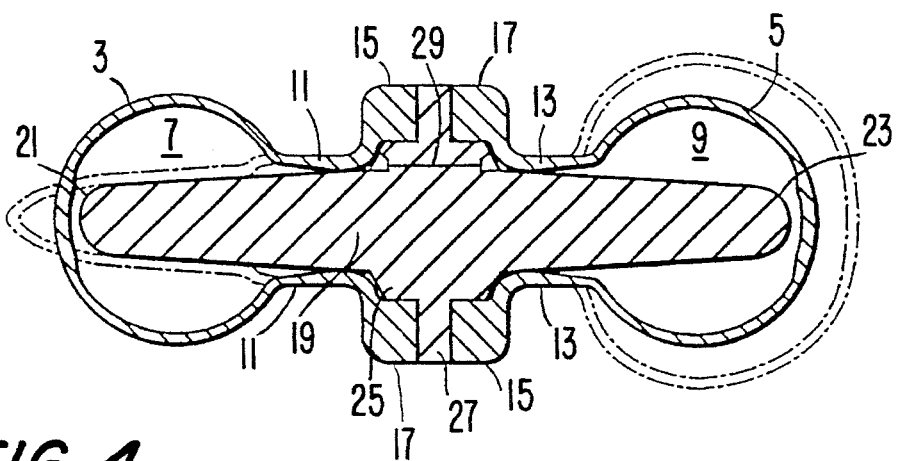
FIG. 2
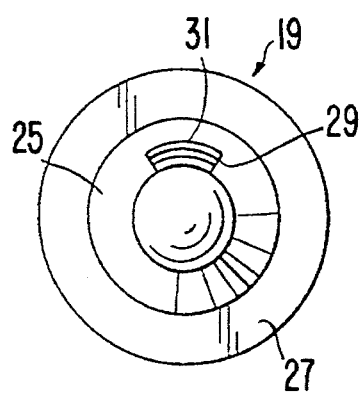
FIG. 4
FIG. 3

EARPLUG WITH FORM-FITTING FLUID CHAMBERS

BACKGROUND OF THE INVENTION

The present invention relates to ear protective devices, i.e., earplugs. More specifically, the invention concerns earplugs of the fluid expansible variety, wherein an earplug element once inserted into the ear can be expanded to obtain a form-fitting seal.

Over the years, a variety of constructions have been proposed for earplugs designed to protect against hearing loss due to excessive noise, and/or to seal off the ear canal and thereby protect the ear from the entry of water, dust, or other potentially harmful matter. A well known class of earplug relies on the deflection of soft rubber flanges, cones, bulbs or like elements to plug the ear canal and hold the plug in place. See, e.g., Watson et al. U.S. Pat. No. 2,437,490; Knudsen U.S. Pat. No. 2,246,736; and Ochi et al. U.S. Pat. No. 4,540,063. These types of devices cause pressure points within the ear which can eventually, if not immediately, cause irritation to the user.

In another variety, the earplug consists of a segment of soft foamed plastic material which the user squeezes down to a small diameter and inserts quickly into the ear canal, allowing the foam to expand within the ear canal. See, e.g., Leight U.S. Pat. No. 4,434,794 and Gardner, Jr. U.S. Reissue Pat. No. 29,487. This type of earplug is more comfortable, but is difficult to insert into the ear and often does not retain well. The insertion of this type of earplug into the ear can be likened to pushing on a rope and usually cannot be performed quickly enough before significant expansion has occurred. Moreover, foamed plastic plugs inherently have many pores which trap contaminants and are subject to bacterial growth. As a result, for hygienic reasons, it is generally recommended that foamed plastic earplugs be discarded after only a couple of uses.

Attempts have also been made to construct form-fitting earplugs using resiliently expansible chambers filled/fillable with a fluid such as a gas or a liquid, or a viscous material such as a paste, gel or putty.

In Mills U.S. Pat. No. 3,736,929, a dumbbell shaped elastic envelope contains a viscous filler such as a soft wax, gel, plastic or silicone putty. Two cavities are connected by a restricted passageway ("commissure"). The plug is inserted into the ear by squeezing down one cavity (and simultaneously expanding the other cavity) and inserting the squeezed down cavity into the ear canal. The elasticity of the envelope thereafter causes the filler material to flow back into the squeezed down cavity so that the outer wall thereof expands into sealing contact with the ear canal. With this design, the expansion force of the inserted cavity against the ear canal is fixed by the characteristics of the filler material and the envelope. Since independent control of the expansion degree by the user is not possible, the result may be an expansion force insufficient to create a good seal, or an excessive expansion force resulting in user discomfort. Moreover, given the criticality of the flow characteristics of the filler material, the design does not allow for use of relatively inexpensive liquid or gaseous fillers.

Wasserman U.S. Pat. No. 2,876,767 discloses an earplug having a resilient bladder that is inflatable with air once inserted into the ear. A one-way valve assembly incorporated into each earplug, and a separate syringe, are required to accomplish the inflation. A valve arrangement is also provided for allowing air to escape from the bladder. In addition to its obvious structural complexity, this design would be difficult to use, e.g., due to the required manipulation of a separate filling tool (syringe) before each use.

Akiyama U.S. Pat. No. 4,060,080 discloses an earplug with a pair of resilient fluid-filled chambers. Once an insertion end of the plug is inserted into the ear canal, a fluid contained in a first chamber at an opposite end of the plug is squeezed into a second chamber at the insertion end, whereby the insertion end is expanded. Catch means are provided for maintaining the first chamber in a collapsed condition so that the second chamber remains inflated. With this arrangement, the degree of filling of the second chamber is not adjustable to suit the individual user—the first chamber must always be collapsed to the same position. An uncomfortable fit or inadequate seal may thus result.

Michael et al. U.S. Pat. No. 2,824,558 likewise discloses an earplug having a pair of resilient fluid chambers, wherein once an insertion end of the plug is inserted into the ear canal, a fluid contained in a storage chamber at an opposite end of the plug is squeezed into a second chamber at the insertion end. Rather than employing a catch in order to maintain the first chamber in a collapsed condition, the Michael et al plug utilizes a resilient one-way check valve that opens responsive to increased pressure generated in the storage chamber upon squeezing the same, then closes to maintain the second chamber in an expanded condition. While advantageously allowing a user to adjust the degree of filling of the second chamber, the design suffers from a disadvantage in that the valve arrangement is relatively complex. It also requires a preliminary pressure release step when it is desired to remove the earplug.

An additional limitation of all of the valved earplugs discussed above is their unidirectional nature, i.e., the plugs all have a specific insertion end. Since the plug can be inserted from one end only, manipulation of the plug into the single proper insertion orientation is required before insertion.

SUMMARY OF THE INVENTION

It is a principal object of the present invention to provide an earplug that is easily properly inserted, that provides a reliable seal of the ear canal, and that provides a comfortable fit allowing the earplug to be worn for a number of hours without irritation.

It is a more specific object of the present invention to provide an earplug that is easily adjustable by the user to accommodate different ear canal sizes and shapes, to thereby provide a custom fit.

A further object of the present invention is to provide an earplug with bi-directional insertability, i.e., having two opposite ends, either one of which is equally suited for insertion into the ear.

Another object of the invention is to provide an earplug designed to minimize the risk of injury to the ear during insertion, use and removal of the earplug.

Still another object of the invention is to provide an earplug that provides a reasonably high degree of sound attenuation.

Yet another object of the present invention is to provide an earplug of simple, inexpensive and long-lasting construction.

These and other objects of the invention are achieved with an ear protective device in accordance with the present invention.

In one aspect, the ear protective device has an outer body defining two resiliently expansible and collapsible fluid chambers, and a quantity of fluid sealed within the outer body. (In addition to those fluids commonly recognized as fluids, such as water or air, the term herein is meant to also include non-Newtonian fluids such as gels, pastes, putty, etc.) An elongated relatively rigid core member extends within the outer body and serves to facilitate insertion of at least one of the fluid chambers into an ear canal. A passageway is defined between the two fluid chambers for selectively placing the fluid chambers in fluid communication with each other. A two-way pressure responsive valve arrangement is operative to close off the passageway and thereby isolate the fluid chambers from each other so as to maintain an equilibrium condition with one of the chambers expanded and the other of the chambers substantially collapsed. The valve arrangement is further operative to temporarily open the passageway when an expanded one of the fluid chambers is squeezed, thereby collapsing the expanded chamber and allowing the fluid therein to pass into and expand the other chamber.

In another aspect of the invention, the ear protective device is bi-directionally insertable and has an outer body defining two resiliently expansible and collapsible fluid chambers, and a quantity of fluid sealed within the outer body. Each chamber is sized and configured for insertion and expansion inside of an ear canal. A passageway is defined between the two fluid chambers for selectively placing the fluid chambers in fluid communication with each other. A two-way pressure responsive valve arrangement is operative to close off the passageway and thereby isolate the fluid chambers from each other so as to maintain an equilibrium condition with one of the chambers expanded and the other of the chambers substantially collapsed. The valve arrangement is further operative to temporarily open the passageway when an expanded one of the fluid chambers is squeezed, thereby collapsing the expanded chamber and allowing the fluid therein to pass into and expand the other chamber.

In preferred embodiments, the valve arrangement comprises an elastically displaceable elastomeric wall bounding the passageway between the chambers. Although many different fluids, including gels, pastes, putty, etc., may be used, the fluid is most preferably a gas, e.g., air.

The inventive earplugs described herein have the ability to be properly inserted (from either end) into the ear canal, and to provide a comfortable fit that allows them to be worn for several hours without irritation. The plugs conform to different sizes and shapes of ear canals with an equi-pressure conforming surface. Pressure points that can cause irritation are avoided. The earplugs assume their usage shape after insertion into the ear canal, under user control. This is accomplished with a simple two-way pressure responsive valve arrangement formed by the injection molded elastomeric earplug body. Proper insertion of the inventive plugs into the ear canal is greatly assisted by a semi-rigid rubber core member extending within the outer body of the earplug. Also, since the earplugs are molded of a smooth surfaced elastomer, they are washable and can be reused over and over.

These and other objects, features and advantages of the invention will be apparent and fully understood from the following Detailed Description of the Preferred Embodiments, taken in connection with the appended drawings.

BRIEF DESCRIPTION OF THE DRAWINGS

FIG. 1 is a perspective view of a form-fitting earplug in accordance with the present invention.

FIG. 2 is a longitudinal cross-sectional view of the earplug shown in FIG. 1.

FIG. 3 is a cross-sectional view of a core member of the earplug shown in FIGS. 1 and 2.

FIG. 4 is an end elevational view of the core member shown in FIG. 3.

DETAILED DESCRIPTION OF THE PREFERRED EMBODIMENTS

Figure 5:
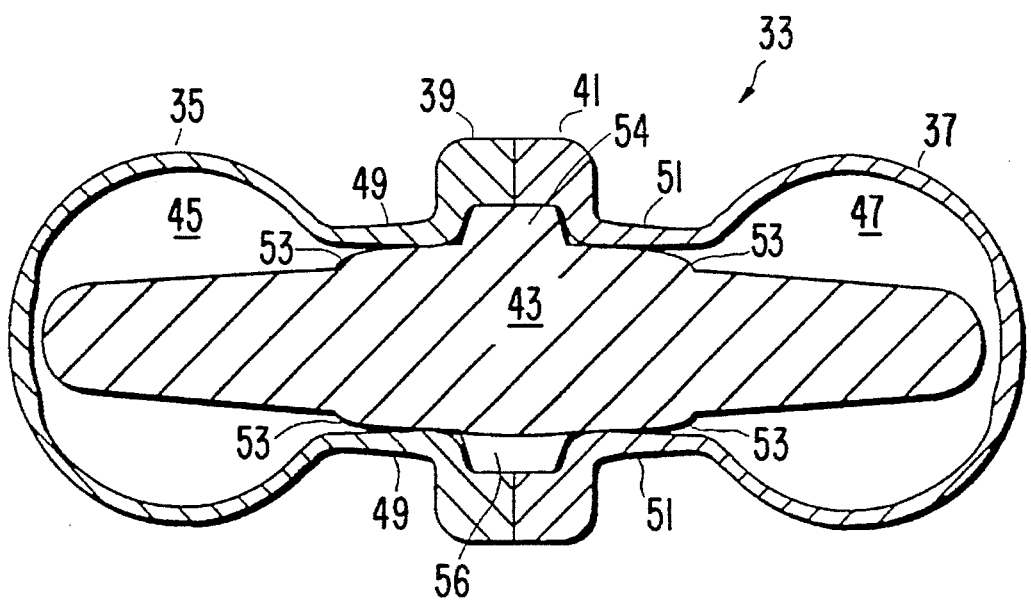
FIG. 5 is a longitudinal cross-sectional view of a second earplug embodiment of the present invention.

FIGS. 1–4 illustrate a first preferred earplug embodiment in accordance with the present invention. Earplug 1 has an outer body comprising a pair of spaced bulbs 3,5 at its opposite ends. With reference to FIG. 2, bulbs 3,5 define a pair of resilient fluid chambers 7,9. A quantity of fluid is sealed within the earplug outer body and is transferable between chambers 7,9 to selectively collapse and expand the same. Although various gases, liquids, gels, or pastes could be used, air is preferred as the filling material since it is readily available, easy to fill in the chambers, and perfectly safe in the case of leakage. Generic references herein to a "fluid" will be understood to encompass all of the aforementioned possible filling materials.

In use, a collapsed end of plug 1 (the left end as depicted by the phantom lines in FIG. 2) is inserted into the ear canal. Once in position, the opposite bulb outside of the ear is squeezed with the fingers to expel the air (or other fluid) therefrom and thereby expand the internal bulb to seal off the ear canal and hold the plug comfortably in place. By squeezing the bulb to different degrees, the user may adjust the sealing pressure and obtain a custom fit.

The inflated bulb remains inflated when the fingers release the collapsed bulb, by way of a novel two-way pressure responsive valve to be described in detail hereinafter. With slight pressure exerted on the inflated bulb, however, the valve will open and allow the fluid in the expanded chamber to be expelled to the other chamber.

When expanded, the inserted bulb should seal in a rearward part of the ear canal having a somewhat larger cross-sectional area than the entrance to the canal. As a result, the plug is retained well inside of the ear until it is desired to remove it. When desired, earplug 1 can be easily removed from the ear by a slight tug on the exposed end. As the expanded bulb inside of the ear is pulled outwardly, it is squeezed by the narrowing ear canal walls and caused to deform and deflate to a size allowing it to pass easily out of the ear.

When inflated, each bulb, like a common balloon, may be compressed and distorted around its circumference to conform to an irregular cross-sectional shape of an ear canal. Since very few ear canals are round in cross-section (most are uniquely irregular, oblong, or even somewhat "slotted" in shape) the ability of the inventive earplugs to conform closely to a wide range of shapes is important to creation of a good seal within the ear canal, and also to fit comfortably with an equi-pressure surface—unlike the conventional earplugs that rely on mechanical distortion of solid earplug elements.

Strictly speaking, it is only necessary that one of the bulbs be sized and configured for insertion into an ear canal. The other bulb may be of any shape so long as the fluid contained therein and expellable therefrom is of a proper amount to inflate the bulb positioned within the ear. In the illustrated preferred embodiments, the two bulbs are made identical so that the plug is bi-directionally insertable, i.e., either bulb may be inserted into the ear. This provides a high degree of convenience.

Moreover, the use of two identical parts facilitates the manufacture and assembly of the earplug, since fewer parts and tools are required. The outer body of plug 1 is formed of two identical parts, each having a relatively thin walled portion forming the bulbs 3,5 and necked portions 11, 13 attached thereto, and a relatively thick-walled portion forming annular mounting flanges 15, 17. With one part design instead of two, the storage and sorting of parts is simplified. The types of part feeding equipment to be used in the assembly is also reduced.

Although the shape of bulbs 3,5 is shown as spherical, the bulbs could be elongated, e.g., ellipsoidal or partly cylindrical in shape. A circular cross-section is desirable so that the device can be inserted into the ear without regard to orientation. The surface of the bulbs should be smooth, i.e., without irregularities that could prevent the formation of a good seal. A smooth non-porous elastomeric surface will also allow the earplugs to be easily washed (sanitized) and reused.

To facilitate the insertion of a deflated one of bulbs 3,5 into the ear canal, a semi-rigid core member 19 extends within the outer body, substantially from one end to the other. Core member 19 is rod-like, having a circular cross-section and tapering slightly from its longitudinal center to blunted ends 21, 23. The slight taper serves two primary purposes. First, it facilitates removal of the part from the mold. In this respect, one side may be given a slightly smaller taper so that the part remains in a specified mold halve (at mold separation) from which it can then be ejected. Secondly, the taper allows the bulbs to collapse to a greater degree while maintaining the rigidity of the core member, as shown generally by the phantom lines in FIG. 2, thereby facilitating proper insertion of the earplug into the ear canal. The core member material should be firm enough to lend rigidity to the otherwise flimsy deflated bulb, yet soft enough so that any excess insertion force causes the core to collapse or bend over, rather than continue into the ear and possibly cause injury. While the tapered end of the core member on the side of a deflated bulb allows the deflated bulb to be pushed into the ear canal, the tapered end on the opposite side provides a semi-rigid means to be pushed on by the thumb for insertion. This makes it unnecessary to lift up on the ear with the other hand to accomplish insertion as required by many earplug designs.

At the longitudinal center of core member 19 is formed a radially extending flange. The flange has a relatively wide base portion 25 and a relatively narrow outer portion 27. The opposite sides of outer portion 27 provide mounting surfaces for attachment of the annular mounting flanges 15,17 of the two outer body parts. By abutting against mounting flanges 15, 17 (which in use are sized to abut against the outer ear) the flange of core member 19 also serves to assure that the plug is not inserted too far into the ear; it acts as a stop that causes the back half of the core to collapse if earplug 1 is pushed into the ear too hard.

The controlled transfer of fluid from one chamber 7,9 to the other is effected through a passageway defined between the two chambers, and a two-way pressure responsive valve formed in base portion 25 of core member 19. The passageway is defined at its ends between the core member 19 and the necked portions 11, 13 of the two outer body parts. In the embodiment of FIGS. 1–4, the necked portions 11, 13 are sized sufficiently larger in diameter than the corresponding parts of the core member 19 so that the fluid can pass readily therebetween.

A central part of the passageway is defined by a slit (or other shaped puncture) 29 extending longitudinally from one side of base portion 25 to the other. Slit 29 can be formed with a fine blade or needle after core member 19 has been molded. Circumferential recesses or cut-outs 31, shown extending through an arc of about 60° (see FIG. 4), are formed in base portion 25 for several reasons. As seen most clearly in FIG. 3, slit 29 opens into recesses or cut-outs 31 so that slit 29 is not obstructed by the abutting inside wall surfaces of flanges 15, 17. Recesses 31 also serve as a location means for performing the secondary operation of creating a slit or puncture, and to protect the end openings of slit 29 from exposure to solvent or adhesive during bonding of the earplug pieces.

The material of core member 19 should be chosen such that the elasticity thereof normally maintains the walls bounding slit 29 tightly together to seal off the passageway. However, when sufficient fluid pressure is developed on either side of slit 29, the elasticity of the core member material should allow the walls of the slit to separate and fluid to pass therethrough.

In this manner, slit 29 serves as a two-way pressure responsive valve operative to close off the passageway and thereby isolate chambers 7, 9 from each other. The closing force should be such as to maintain an equilibrium condition with one of chambers 7,9 expanded and the other substantially collapsed, as illustrated by the phantom lines in FIG. 2. The valve formed by slit 29 should further be operative to temporarily open the passageway when an expanded one of chambers 7,9 is squeezed, to thereby allow the expanded chamber to collapse and the fluid therein to pass into and expand the other chamber. In order to optimize the opening characteristics of the slit, the longitudinal and circumferential dimensions thereof may be varied. A small needle puncture hole may be used as an alternative to a slit. Suitable materials for the two outer body parts, and the core member 19, include elastomeric rubbers and silicone based materials. Preferably, the earplug parts are injection molded of an FDA approved thermoplastic elastomer. These materials, unlike conventional rubbers, silicones and the like, can be injection molded at low cost and allow more flexibility in the methods used to bond the pieces together.

In particular, a thermoplastic rubber marketed by Shell Chemical Company under the name KRATON is preferred because of its resilience, strength and durability, and its ability to form a strong and reliable solvent bond (e.g., using Toluene as the solvent). A specific KRATON compound used with good results is designated by Shell in its Technical Bulletin (SC:1032-88) as G-2706. As explained in that publication, the G-2700 KRATON compounds are based on styrene-ethylene/butylene-styrene copolymers with a very stable saturated midblock. Another potentially suitable thermoplastic rubber is sold by Monsanto under the name SANTOPRENE.

A suitable Shore A durometer of the core member material is 45. This provides sufficient rigidity to the core to allow insertion yet allows collapse under excess insertion force, thereby preventing injury to the ear. The thermoplastic rubber of the bulb is preferably somewhat softer, e.g., having a Shore A durometer of 30. KRAYTON is available in these different hardnesses.

Although solvent bonding is preferred, various other bonding methods may be utilized, such as adhesive bonding. The key is that a strong and durable fluid tight seal be obtained.

To produce a finished earplug using solvent bonding, toluene solvent is carefully applied to the mating surfaces of mounting flanges 15, 17, and core flange part 27. Then, the respective pieces are assembled together as shown in FIG. 2 and tightly clamped for a sufficient time (e.g., 5–15 minutes) to allow the mating surfaces to fuse and cure.

A convenient clamping arrangement comprises two metal plates hinged to each other and having aligned apertures. The apertures are sized to allow the collapsed bulbs to pass therethrough and flanges 15, 17 to rest on the plates about the perimeters of the apertures. After the bulbs are positioned in the plates, core member 19 is inserted into one of the bulbs, then the plates are pivoted toward each other to mate the parts. The plates can then be clamped together in a folded condition with the parts pressed tightly together.

At the time of assembly, one of the bulbs may be squeezed and thereby held in a collapsed or semi-collapsed condition while the other is allowed to assume a natural expanded but unstretched state. In this manner, the amount of air sealed in the earplug is reduced. In use, when one bulb is squeezed, the other will be filled only to its natural expanded but unstretched condition, or to a just slightly stretched condition. This approach helps ensure that the chambers are not overinflated within the ear, thus minimizing the possibility of rupture of the inflated bulb. Alternatively, the bulbs could be assembled while both are allowed to assume their naturally expanded but unstretched states. In this case, in use, when one bulb is collapsed by squeezing, the other will be expanded to approximately twice its original volume, to a stretched state as depicted by the phantom lines in FIG. 2 (bulb 5). A range of size adjustability is provided somewhat by the extent of inflation, but more so by the ability of the bulbs to change their longitudinal dimension in response to varying sizes of ear canal cross-section.

With the present inventive earplugs, long-term air loss due to the gas permeability of the thermoplastic rubber walls is generally not a significant problem, due to the relatively small pressure differentials developed between the inside and outside of the bulbs. Significant air seepage is likely to occur only if an earplug is left to sit for an extended period (e.g., several days) with one of bulbs expanded to a stretched condition. In this case, air seepage may cause the expanded bulb to return to an unstretched condition whereby air would still be transferable between the bulbs to achieve alternating expansion of the chambers up to the natural expanded but unstretched state of the bulbs. If the earplug is sized to seal a large ear canal in its natural expanded but unstretched state, then the ability to expand the bulbs to a larger (stretched) size is not required.

The invention also contemplates the use of fluid filler and bulb material combinations that are highly resistant to fluid permeation. Such combinations as are known, e.g., in the athletic shoe arts, would be particularly desirable if a filling degree is chosen that results in significant expansion of the bulbs beyond their natural expanded condition.

Good results have been obtained by injection molding core member 19 with the parting line of the mold, and the mold gate, located along the outer circumference of flange portion 27. A circumferential parting line about flanged portion 27 is preferred over a longitudinal parting line, since the latter may adversely affect the seals between core flange portion 27 and bulb mounting flanges 15, 17. Good results have been obtained by injection molding the outer body parts (bulbs) with the mold parting line arranged to extend about mounting flanges 15, 17, and by positioning the mold gate at the longitudinal center of the thin-walled bulbs 3, 5.

The wall thicknesses of bulbs 3, 5 should be chosen taking into account the opposing considerations of strength and durability on one hand, and resilience on the other. Unlike a common balloon, the walls should be sufficiently firm to maintain their natural bulbous shape when the fluid pressure on the inside and out is equal. It has been found that good results are obtained with a wall thickness of 0.14±0.002 inches. A slightly thicker region should be provided adjacent the gate location to (1) counter any weakening of the thin wall due to a possible discontinuity formed by the gate, (2) assist with material flow during molding, and (3) minimize the chance of rupture caused by the blunted core ends 21, 23 pressing against the bulb walls during insertion.

Figure 7:
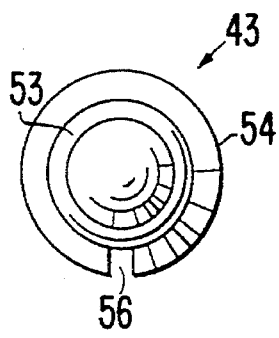
FIG. 7 is an end elevational view of the core member shown in FIG. 6.
Figure 6:
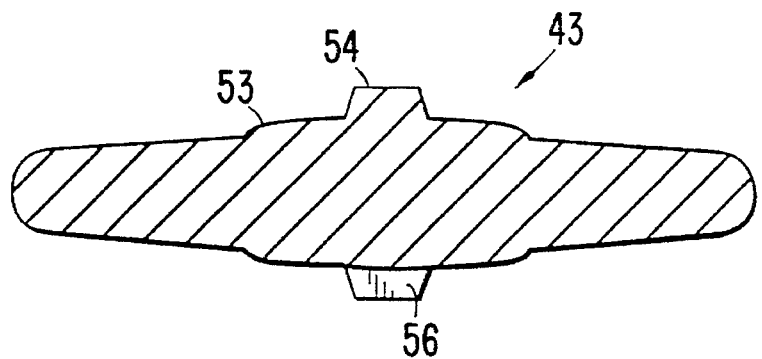
FIG. 6 is a longitudinal cross-sectional view of a core member of the earplug shown in FIG. 5.

Referring now to the second embodiment illustrated in FIGS. 5–7, earplug 33 differs from earplug 1 in that a pair of bulbs 35, 37 are attached directly to each other at mating ranged ends 39, 41, to seal within the outer plug body a semi-rigid core member 43. In this embodiment, a releasable seal between fluid chambers 45, 47 is formed by necked portions 49, 51 of the two outer body parts being stretched over an enlarged diameter part 53 of the core. Squeezing pressure exerted on an inflated bulb causes the necked portions 49, 51 to stretch and break the seals on both sides to allow the air (or other fluid) to pass from one chamber to the other. The core member 43 of this embodiment has a radial central flange 54 that abuts with the inner surfaces of mounting flanges 39, 41 to prevent excessive insertion of core member 43 into the ear canal. Flange 54 is truncated so as to be wholly contained within the outer body formed by the bulb halves. A slot 56 is provided through radial flange 54 to allow fluid to flow freely therethrough.

As in the first embodiment, core member 43 is preferably injection molded with a circumferential parting line extending about central flange 54. A longitudinal parting line would extend across the locations where the necked portions 49, 51 are stretched over the enlarged core part 53, and make formation of a reliable valve seal more difficult. In this embodiment, the provision of a single bond location of the outer body parts (bulbs) to each other minimizes the possibility of fluid leakage to the outside.

Figure 8:
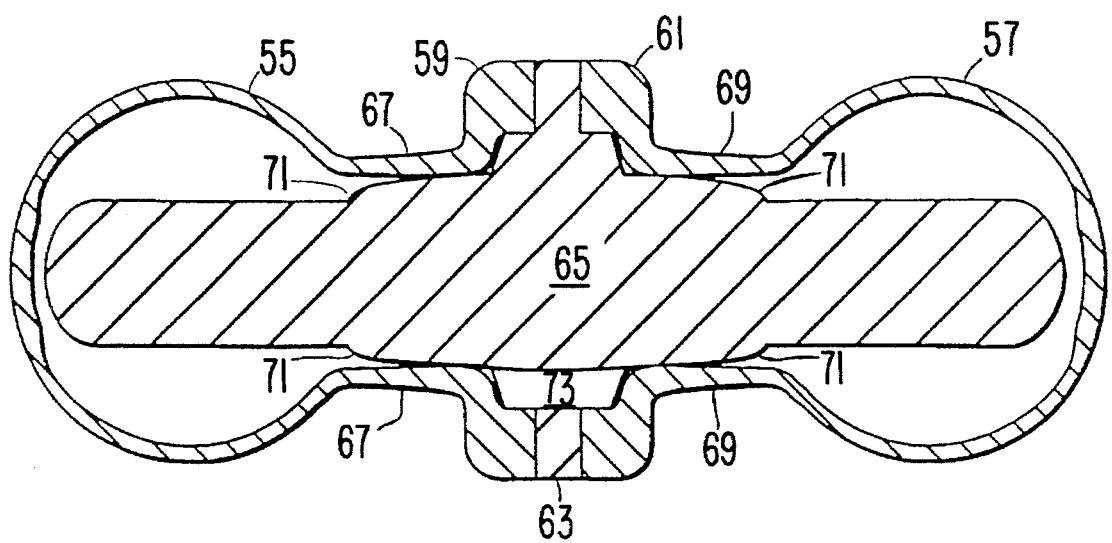
FIG. 8 is a longitudinal cross-sectional view of a third earplug embodiment of the present invention.

The third embodiment illustrated in FIG. 8 includes a combination of the features shown in the first two embodiments. Namely, as in the first embodiment, two bulbs 55, 57 are bonded at flanged ends 59, 61 to opposite sides of a stepped radial flange 63 of a core member 65. As in the second embodiment, a two-way pressure responsive valve is formed by necked portions 67, 69 of bulbs 55, 57 being stretched over an enlarged diameter central part 71 of the core member 65. In this embodiment, to allow air to pass from one side to the other, a slot 73 is provided through radial flange 63. As a further variation, flange 63 could be pierced with a fine blade or needle (instead of being slotted) to act as a supplemental two-way pressure responsive valve.

Figure 9:
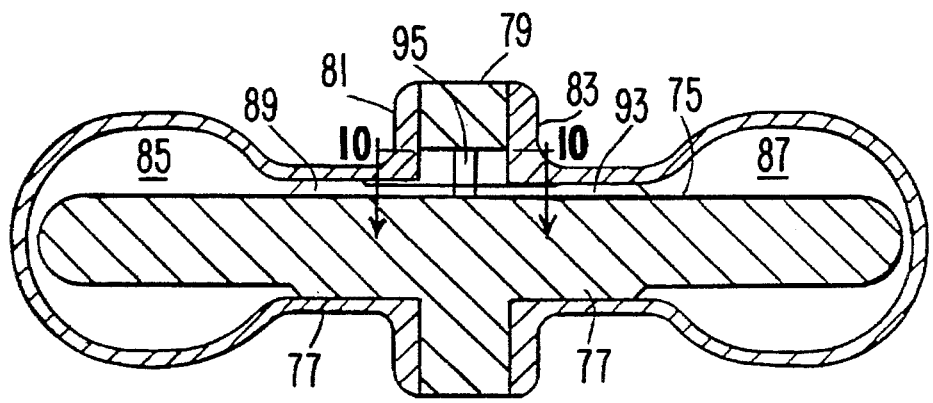
FIG. 9 is a longitudinal cross-sectional view of a forth earplug embodiment of the present invention.
Figure 10:
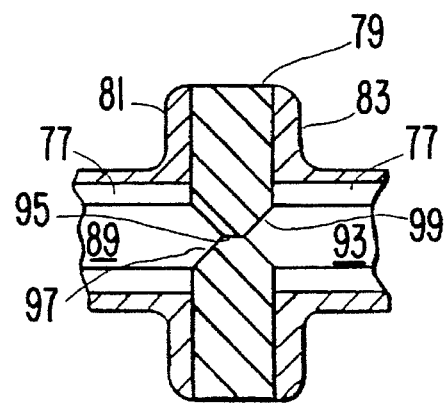
FIG. 10 is a broken-away cross-sectional view taken on line 10—10 in FIG. 9.

Referring now to the fourth embodiment of FIGS. 9 and 10, an internal core member 75 has an enlarged diameter central part 77 and a relatively wide radial flange 79 to which the mounting flanges 81, 83 of the outer body parts are attached on opposite sides. A passageway is formed between fluid chambers 85, 87 by a pair of slots 89, 93 extending through core central part 77. A two-way pressure responsive valve serving to selectively seal-off chambers 85, 87 is formed by a slit 95. Slit 95 extends radially and longitudinally between a pair of V-shaped recesses 97, 99 (best seen in FIG. 10) provided on either side of radial flange 79. By varying the depth of recesses 97, 99, and thereby the length of slit 95, the force (fluid pressure) required to open the two-way valve can be optimized.

Figure 11:
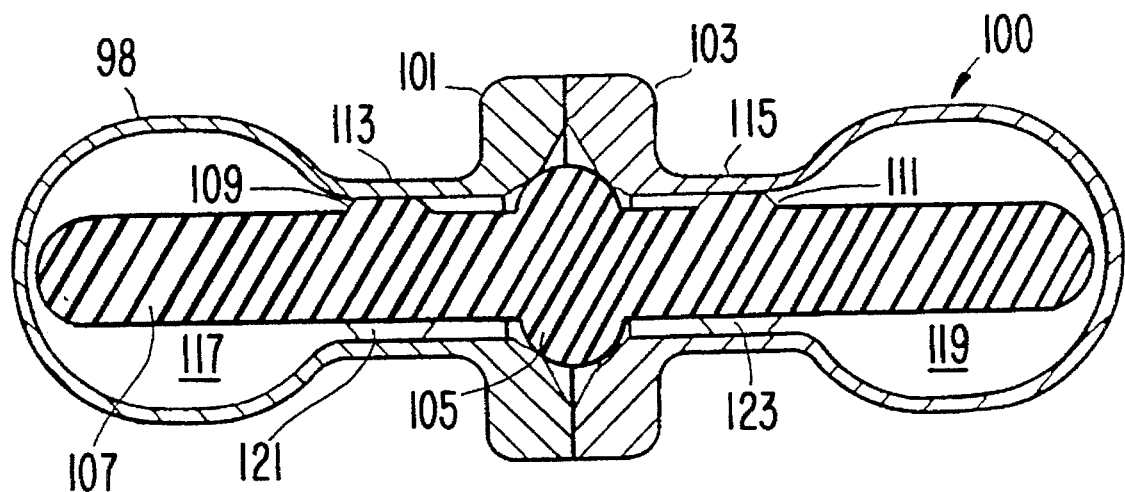
FIG. 11 is a longitudinal cross-sectional view of a fifth earplug embodiment of the present invention.

Referring now to the fifth embodiment of FIG. 11, as in the embodiment of FIG. 5, the two bulbs 98, 100 are secured directly to each other at flanged ends 101, 103. Here, however, the inner surfaces of flanged ends 101, 103 cooperate with a bead-shaped midpart 105 of a core member 107 to form a two-way pressure responsive valve. Flanged ends 101, 103 and core midpart 105 are sized with respect to each other such that the flanged ends are stretched to fit over midpart 105 to create a seal that can be broken by the fluid pressure developed by squeezing one of the bulbs. Two spaced enlarged diameter portions 109, 111 are provided on the core member 107, on either side of the midpart 105, to help support core member 107 within the outer body parts, and at the same time ensure that clear passageways are maintained between the core member 107 and necked portions 113, 115. A clear passage through portions 109, 111 is provided by slots 121, 123 extending therethrough.

As shown, enlarged diameter portions 109, 111 would require core member 107 to be injection molded with a longitudinally extending mold parting line, in order to allow removal of the part from the mold. To allow molding with a centered circumferential mold parting line (that would avoid potential interference with formation of a good seal between midpart 105 and flanged ends 101, 103), enlarged diameter portions 109, 111 could be reconfigured to extend continuously (preferably with a slight taper) from midpart 105, similar to enlarged diameter part 53 of the FIG. 5 embodiment.

Figure 12:
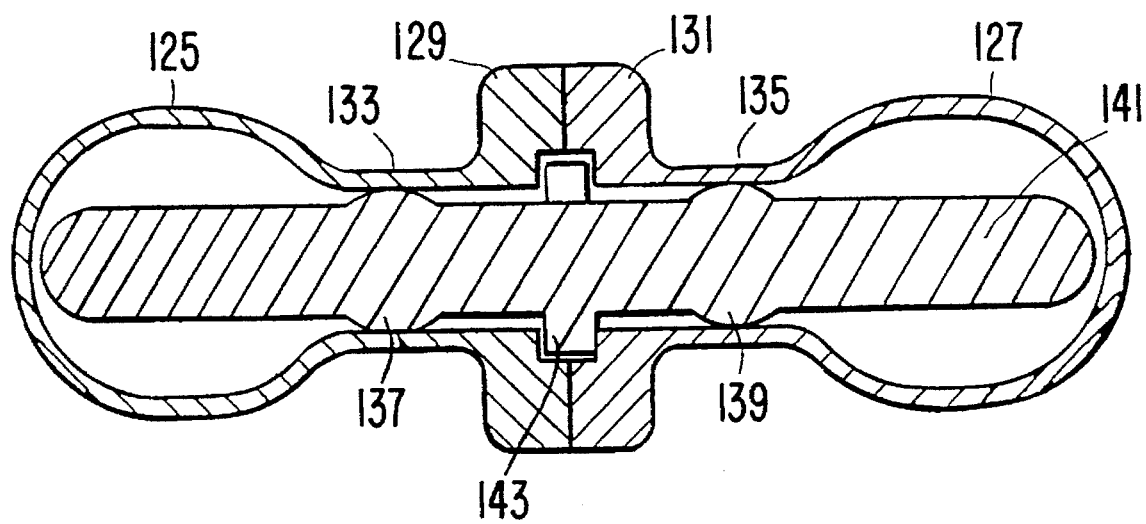
FIG. 12 is a longitudinal cross-sectional view of a sixth earplug embodiment of the present invention.

The sixth embodiment of FIG. 12 is similar to the embodiment of FIG. 5 in that a pair of bulbs 125, 127 are attached directly to each other at flanged end portions 129, 131 and in that a pair of two-way pressure responsive valves are formed by necked portions 133, 135 of the outer body parts being stretched over enlarged parts 137, 139 of core member 141. In this embodiment, however, enlarged parts 137 and 139 are formed to have an arcuate bead-like shape, similar to midpart 105 of the FIG. 11 embodiment. Central flange 143 serves the same purpose as flange 54 in the FIG. 5 embodiment, but is shaped without a taper. The FIG. 5 embodiment is preferred over the FIG. 12 embodiment since only the former can be injection molded with a centered circumferential parting line. As previously mentioned, a circumferential parting line will avoid potential interference with formation of a good seal at the two-way pressure valves.

Figure 13:
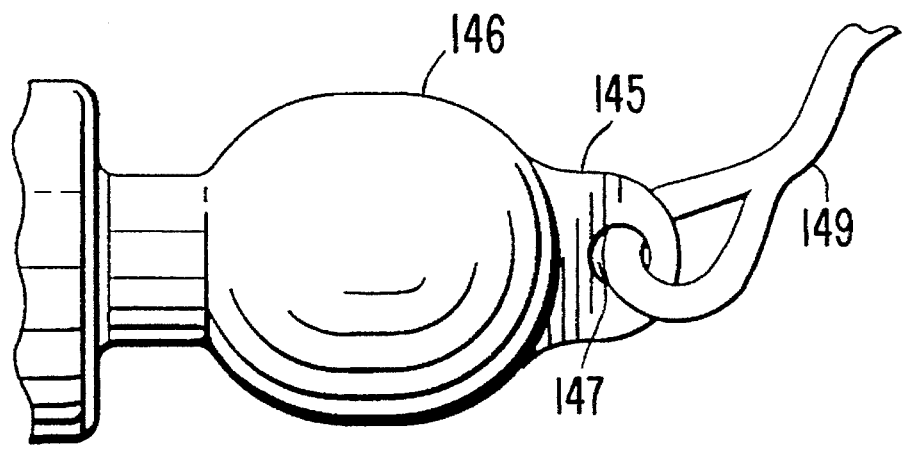
FIG. 13 is a broken-away side elevational view of a first earplug cord attachment arrangement in accordance with the present invention.
Figure 14:
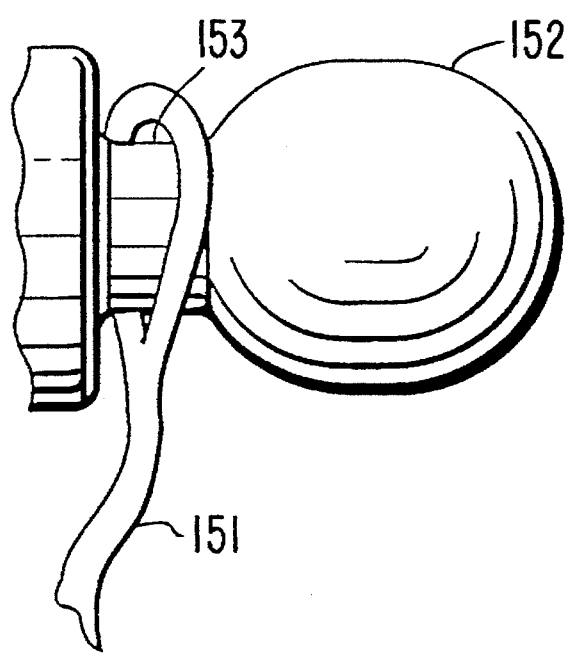
FIG. 14 is a broken-away side elevational view of a second earplug cord attachment arrangement in accordance with the present invention.

Referring now to FIGS. 13 and 14, alternative configurations are shown for attaching a lanyard between a pair of the inventive earplugs. Such an arrangement allows the earplugs to hang about a person's neck when not in use, whereby they can be easily located and inserted into the ears when necessary. In the embodiment of FIG. 13, an attachment flange 145 is integrally molded to one of the bulbs 146. The flange has a hole 147 through which a lanyard 149 can be looped. In the embodiment of FIG. 14, a lanyard 151 (which could be elastic) is simply looped over one of the bulbs 152 and is held on necked portion 153 extending from bulb 152.

The present invention has been described in terms of preferred embodiments thereof. Other embodiments and variations within the scope of the appended claims will be apparent to those of ordinary skill in the art upon reading this disclosure.

I claim:

1. An ear protective device comprising:

an outer body defining two resiliently expansible and collapsible fluid chambers;

a quantity of fluid sealed within said outer body;

an elongated relatively rigid core member extending within said outer body and serving to facilitate insertion of at least one of said fluid chambers into an ear canal;

a passageway defined between said two fluid chambers for selectively placing said fluid chambers in fluid communication with each other;

a two-way pressure responsive valve adjacent said passageway operative to close off said passageway and thereby isolate said fluid chambers from each other so as to maintain an equilibrium condition with one of said chambers expanded and the other of said chambers substantially collapsed, said valve being further operative to temporarily open said passageway when an expanded one of said fluid chambers is squeezed, thereby collapsing said expanded chamber and allowing the fluid therein to pass into and expand the other chamber.

2. An ear protective device according to claim 1, wherein said fluid is a gas.

3. An ear protective device according to claim 2, wherein said gas is air.

4. An ear protective device according to claim 1, wherein said valve comprises an elastically displaceable elastomeric wall bounding said passageway.

5. An ear protective device according to claim 4, wherein said passageway extends within said core member and said elastomeric wall comprises an internal surface of said core member.

6. An ear protective device according to claim 4, wherein said passageway extends between said core member and said outer body, and said elastomeric wall portion comprises an internal surface of said outer body resiliently maintained against an outer surface of said core member.

7. An ear protective device according to claim 6, wherein said valve arrangement comprises a necked portion of said outer body stretched over an enlarged portion of said core member.

8. An ear protective device according to claim 1, wherein said outer body is formed in two pieces, each piece comprising an elastomeric bulbous portion defining a said fluid chamber, and an annular end mounting flange attached thereto, the annular end mounting flanges of the first and second pieces being fixed with respect to each other in an opposed relationship.

9. An ear protective device according to claim 8, wherein said two pieces of the outer body are identical to each other.

10. An ear protective device according to claim 8, wherein said core member comprises an annular center mounting flange intermediate its ends, and said annular end mounting flanges are secured together on opposite sides of said center mounting flange.

11. An ear protective device according to claim 10, wherein the two pieces of said outer body and said core member are formed of thermoplastic rubber, and said end mounting flanges are solvent-bonded to opposite sides of said center mounting flange.

12. An ear protective device according to claim 8, wherein said annular end mounting flanges are secured directly to each other.

13. An ear protective device according to claim 12, wherein the two pieces of said outer body are formed of thermoplastic rubber and said annular end mounting flanges are solvent-bonded to each other.

14. An ear protective device according to claim 5, wherein said passageway extends through a base portion of said center mounting flange, and said elastomeric wall portion comprises an internal surface of said base portion.

15. An ear protective device according to claim 14, wherein said annular base portion is provided with a recess on each of opposite sides thereof, and said passageway opens into said recesses.

16. An ear protective device according to claim 14, wherein said passageway comprises a thin slit extending through said base, said slit being elastically openable and closeable in response to varying pressures in said fluid chambers.

17. An ear protective device according to claim 14, wherein said passageway comprises a small puncture through said base, said puncture being elastically openable and closeable in response to varying pressures in said fluid chambers.

18. An ear protective device according to claim 1, wherein said outer body and said core member are injection molded of thermoplastic rubber, said core member having a higher durometer value than said shell member.

19. An ear protective device according to claim 1, wherein said quantity of fluid is such that when one of the chambers is collapsed, the other is filled to an expanded but essentially unstretched state.

20. An ear protective device according to claim 1, wherein said quantity of fluid is sufficiently large to alternatively expand said chambers to a stretched condition.

21. A bi-directionally insertable ear protective device comprising:

an outer body defining two resiliently expansible and collapsible fluid chambers, each chamber being sized and configured for insertion and expansion inside of an ear canal;

a quantity of fluid sealed within said outer body;

a passageway defined between said two fluid chambers for selectively placing said fluid chambers in fluid communication with each other; and a two-way pressure responsive valve adjacent said passageway operative to close off said passageway and thereby isolate said fluid chambers from each other so as to maintain an equilibrium condition with one of said chambers expanded and the other of said chambers substantially collapsed, said valve being further operative to temporarily open said passageway when an expanded one of said fluid chambers is squeezed, thereby collapsing said expanded chamber and allowing the fluid therein to pass into and expand the other chamber.

22. An ear protective device according to claim 21, wherein said valve comprises an elastically displaceable elastomeric wall bounding said passageway.

23. An ear protective device according to claim 22, wherein said fluid is a gas.

24. An ear protective device according to claim 23, wherein said gas is air.

25. An ear protective device according to claim 22, further comprising an elongated core member extending within said outer body, said passageway extending between said core member and said outer body, and said elastomeric wall portion comprising an internal surface of said outer body resiliently abutting against an outer surface of said core member.

26. An ear protective device according to claim 22, wherein said outer body is injection molded of thermoplastic rubber.

27. An ear protective device according to claim 21, wherein said outer body is formed in two pieces, each piece comprising an elastomeric bulbous portion defining a said fluid chamber, and an annular end mounting flange attached thereto, the annular end mounting flanges of the first and second pieces being fixed with respect to each other in an opposed relationship.

28. An ear protective device according to claim 27, wherein the two pieces of said outer body are identical to each other.

29. An ear protective device according to claim 27, wherein said annular end mounting flanges are secured directly to each other.

30. An ear protective device according to claim 29, wherein the two pieces of said outer body are formed of thermoplastic rubber, and said annular end mounting flanges are solvent-bonded to each other.

* * * * *